United States Patent
Dyballa et al.

(10) Patent No.: US 10,196,747 B2
(45) Date of Patent: *Feb. 5, 2019

(54) 2,2'-DIAMINOBIARYLS HAVING TWO SECONDARY AMINES

(71) Applicant: EVONIK DEGUSSA GMBH, Essen (DE)

(72) Inventors: Katrin Marie Dyballa, Recklinghausen (DE); Robert Franke, Marl (DE); Dirk Fridag, Haltern am See (DE); Siegfried R. Waldvogel, Gau-Algesheim (DE); Bernd Elsler, Bonn (DE); Mathias Enders, Hackenheim (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/508,230

(22) PCT Filed: Jul. 23, 2015

(86) PCT No.: PCT/EP2015/066833
§ 371 (c)(1),
(2) Date: Mar. 2, 2017

(87) PCT Pub. No.: WO2016/034330
PCT Pub. Date: Mar. 10, 2016

(65) Prior Publication Data
US 2017/0283961 A1    Oct. 5, 2017

(30) Foreign Application Priority Data
Sep. 3, 2014 (DE) .................. 10 2014 217 540

(51) Int. Cl.
| | |
|---|---|
| C07C 233/44 | (2006.01) |
| C25B 3/10 | (2006.01) |
| C07C 311/21 | (2006.01) |
| C25B 9/06 | (2006.01) |
| C07C 233/43 | (2006.01) |
| C25B 15/02 | (2006.01) |

(52) U.S. Cl.
CPC .............. *C25B 3/10* (2013.01); *C07C 233/43* (2013.01); *C07C 233/44* (2013.01); *C07C 311/21* (2013.01); *C25B 9/06* (2013.01); *C25B 15/02* (2013.01)

(58) Field of Classification Search
None
See application file for complete search history.

(56) References Cited

U.S. PATENT DOCUMENTS

| | | |
|---|---|---|
| 4,528,076 A | 7/1985 | Gossage |
| 2010/0113600 A1 | 5/2010 | Njar et al. |

FOREIGN PATENT DOCUMENTS

| | | |
|---|---|---|
| DE | 2353580 A1 | 5/1975 |
| WO | 2007/129664 A1 | 11/2007 |

OTHER PUBLICATIONS

Wang et al. Tetrahedron 70, 2014, 6879-6884.*
Wuts, P. G. M, et al., Green's Protective Groups in Organic Synthesis, Wiley and Sons, Fourth edition, 2007, pp. 16-366. (351 Pages).
International Search Report dated Jan. 1, 2015 for International Patent Application No. PCT/EP2015/066833 (8 pages with English translation).
Written Opinion dated Jan. 1, 2015 for International Patent Application No. PCT/EP2015/066833 (16 pages with English Translation).
International Preliminary Report on Patentability dated Mar. 7, 2017 International Patent Application No. PCT/EP2015/066833 (18 pages with English Translation).
Search Report for German Patent Application No. 10 2014 217 540.2 dated Jul. 29, 2015 (8 pages in German with standard letter relevance classification).
Cui, et. al. A Concise Synthetic Approach Towards Hydroxytetraphenylenes. Synlett 2011. No. 7. pp. 1018-1022.
Kalk, W. et. al. Ullmann-Reaktionen an ortho-(Acylamino)halogenaromaten. Liebigs Ann. Chem. 1977, pp. 329-337.
Zhang, S. et. al. Ambient Temperature, Ullmann-like Reductive Coupling of Aryl, Heteroaryl, and Alkenyl Halides. Journal of Organic Chemistry. 1997. vol. 62, pp. 2312-2313.
Sayo, H, et al. Anodic Oxidation of Sulfonamides II. Anodic Oxidation of 4'-Substituted Benzenesulfonanilides in Acetonitrile. Chem. Pharm. Bull. 1977. vol. 25 No. 4. pp. 640-646.
Insole, J. M. The circular dichroism of some 2,2'-bridged biphenyls. The absolute configuration of (+)-6,7-diphenyldibenzo[e,g][1,4]diazocine-3,10-dicarboxylic acid. Journal of the Chemical Society C: Organic. 1971. pp. 1712-1715.
Masahiro, Y., et al. Synthesis of 3,3'-Diaryl-Substituted 2,2'-Diamino-1,1'-binaphthyl and Its Derivatives. The Journal of Organic Chemistry. 2010. vol. 75. No. 12. pp. 4315-4318.
Barton, J W, et al. Benzo[c]cinnolines. The Nitration of Benzo[c]cinnoline and its N-Oxide. Journal of the Chemical Society. 1962. pp. 2454-2460.

* cited by examiner

*Primary Examiner* — Ana Z Muresan
(74) *Attorney, Agent, or Firm* — Smith, Gambrell & Russell, LLP (57) ABSTRACT

Novel 2,2'-diaminobiaryls having two secondary amines and an electrochemical process for preparation thereof.

1 Claim, 4 Drawing Sheets

2,2'-DIAMINOBIARYLS HAVING TWO SECONDARY AMINES

The invention relates to novel 2,2'-diaminobiaryls having two secondary amines and to an electrochemical process for preparation thereof.

The direct electrochemical C,C cross-coupling of protected anilines is unknown to date. In the only known couplings, some of which involve toxic reagents, the reactions firstly proceed unselectively and, secondly, large amounts of waste are produced.

It is possible by copper-catalysed C,C coupling to prepare unsymmetric 2,2'-diaminobiaryls in which both amino groups bear the same protecting group (J.-F. Cui, H. Huang, H. Wong, Synlett 2011, 7, 1018-1022). In this context, however, it is particularly disadvantageous that the reaction proceeds very unselectively, and by-products are generated in high yields (>50%). As a result, complex purification steps are additionally necessary, and a large amount of waste (various solvents from the purifications, unwanted by-products) is produced.

Additionally known is the synthesis of symmetrically protected 2,2'-diaminobiaryls having the same protecting groups by an Ullmann-like reaction regime (W. Kalk, H.-S. Bien, K.-H. Schündehütte. Justus Liebigs Ann. Chem. 1977, 329-337, and S. Zhang, D. Zhang, L. S. Liebeskind, J. Org. Chem. 1997, 62, 2312-2313.). The selection of protecting groups and substitution patterns of the substances to be coupled that are used is greatly restricted for this reason. In all cases, an organic oxidizing agent has to be added; in some cases, it is necessary to work with exclusion of moisture or using anaerobic reaction regimes. This fact and the aspect of the additional wastes make it desirable to develop an alternative, inexpensive and more environmentally benign process.

The problem addressed by the invention was that of providing 2,2'-diaminobiaryls having novel structures compared to the 2,2'-diaminobiaryls known in the literature. More particularly, the two amino groups in the 2,2'-diaminobiaryls should also have the same radicals.

In addition, a process by which the novel 2,2'-diaminobiaryls can be prepared in good yield was to be developed. More particularly, the process was to stand out advantageously from the preparation processes known from the prior art.

The object is achieved by a compound according to claim 1.

Compound having one of the general structures (I) to (III):

(I)

(II)

(III)

where
$R^1$, $R^2$, $R^3$, $R^4$, $R^{1'}$, $R^{2'}$, $R^{3'}$, $R^{4'}$ are selected from:
—H, —($C_1$-$C_{12}$)-alkyl, —O—($C_1$-$C_{12}$)-alkyl, —O—($C_6$-$C_{20}$)-aryl, —($C_6$-$C_{20}$)-aryl, halogen, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —COOH, —OH, —$SO_3H$, —CN, —N[($C_1$-$C_{12}$)-alkyl]$_2$;
$R^5$, $R^6$, $R^7$, $R^8$, $R^9$, $R^{10}$, $R^{5'}$, $R^{6'}$, $R^{7'}$, $R^{8'}$, $R^{9'}$, $R^{10'}$ are selected from:
—H, —($C_1$-$C_{12}$)-alkyl, —O—($C_1$-$C_{12}$)-alkyl, —O—($C_6$-$C_{20}$)-aryl, —($C_6$-$C_{20}$)-aryl, —S-alkyl, —S-aryl, halogen, —COO—($C_1$-$C_{12}$)-alkyl, —CONH—($C_1$-$C_{12}$)alkyl, —CO—($C_1$-$C_{12}$)-alkyl, —CO—($C_6$-$C_{20}$)-aryl, —COOH, —OH, —$SO_3H$, —N[($C_1$-$C_{12}$)-alkyl]$_2$;
where the alkyl and aryl groups mentioned may be substituted;
and, in the formula (I), the two radicals of at least one of the four following radical pairs are not the same radical: $R^1$ and $R^{1'}$, $R^2$ and $R^{2'}$, $R^3$ and $R^{3'}$, $R^4$ and $R^{4'}$,
and, in the formula (III), the two radicals of at least one of the six following radical pairs are not the same radical: $R^5$ and $R^{5'}$, $R^6$ and $R^{6'}$, $R^7$ and $R^{7'}$, $R^8$ and $R^{8'}$, $R^9$ and $R^{9'}$, $R^{10}$ and $R^{10'}$,
$X^1$ is selected from:
tert-butyloxycarbonyl, methyloxycarbonyl, benzyloxycarbonyl, phenyloxycarbonyl, trifluoroacetyl, benzoyl, sulphonyl, sulphenyl;
$X^2$ is selected from:
tert-butyloxycarbonyl, methyloxycarbonyl, benzyloxycarbonyl, phenyloxycarbonyl, acetyl, trifluoroacetyl, benzoyl, sulphonyl, sulphenyl;
$X^3$ is selected from:
methyloxycarbonyl, benzyloxycarbonyl, phenyloxycarbonyl, acetyl, trifluoroacetyl, benzoyl, sulphonyl, sulphenyl.

The feature "and the two radicals of at least one of the four following radical pairs are not the same radical: $R^1$ and $R^{1'}$, $R^2$ and $R^{2'}$, $R^3$ and $R^{3'}$, $R^4$ and $R^{4'}$" expresses the fact that this is an unsymmetric biaryl. The two aromatic compounds cannot be reflected onto one another by a mirror plane lying between them.

The following radical pairs are permitted, for example:
$R^1 \neq R^{1'}$, $R^2=R^{2'}$, $R^3=R^{3'}$, $R^4=R^{4'}$;
$R^1=R^{1'}$, $R^2=R^{2'}$, $R^3 \neq R^{3'}$, $R^4=R^{4'}$.

But also radical pairs in which more than just one pair is not the same, for example:
$R^1 \neq R^{1'}$, $R^2=R^{2'}$, $R^3 \neq R^{3'}$, $R^4=R^{4'}$;
$R^1 \neq R^{1'}$, $R^2 \neq R^{2'}$, $R^3 \neq R^{3'}$, $R^4=R^{4'}$.

The only case ruled out is that in which all four radical pairs are each the same radical in pairs:
$R^1=R^{1'}$, $R^2=R^{2'}$, $R^3=R^{3'}$, $R^4=R^{4'}$.

This would be a symmetric biaryl.

The same applies to the following pairs: $R^5$ and $R^{5'}$, $R^6$ and $R^{6'}$, $R^7$ and $R^{7'}$, $R^8$ and $R^{8'}$, $R^9$ and $R^{9'}$, $R^{10}$ and $R^{10'}$.

—$(C_1-C_{12})$-Alkyl and —O—$(C_1-C_{12})$-alkyl may each be unsubstituted or substituted by one or more identical or different radicals selected from —$(C_3-C_{12})$-cycloalkyl, —$(C_3-C_{12})$-heterocycloalkyl, —$(C_6-C_{20})$-aryl, fluorine, chlorine, cyano, formyl, acyl and alkoxycarbonyl.

—$(C_6-C_{20})$-Aryl and —$(C_6-C_{20})$-aryl-$(C_6-C_{20})$-aryl- may each be unsubstituted or substituted by one or more identical or different radicals selected from:
—H, —$(C_1-C_{12})$-alkyl, —O—$(C_1-C_{12})$-alkyl, —O—$(C_6-C_{20})$-aryl, —$(C_6-C_{20})$-aryl, -halogen (such as Cl, F, Br, I), —COO—$(C_1-C_{12})$-alkyl, —CONH—$(C_1-C_{12})$-alkyl, —$(C_6-C_{20})$-aryl-CON[$(C_1-C_{12})$-alkyl]$_2$, —CO—$(C_1-C_{12})$-alkyl, —CO—$(C_6-C_{20})$-aryl, —COOH, —OH, —SO$_3$H, —SO$_3$Na, —NO$_2$, —CN, —N[$(C_1-C_{12})$-alkyl]$_2$.

In the context of the invention, the expression "—$(C_1-C_{12})$-alkyl" encompasses straight-chain and branched alkyl groups. Preferably, these groups are unsubstituted straight-chain or branched —$(C_1-C_8)$-alkyl groups and most preferably —$(C_1-C_6)$-alkyl groups. Examples of —$(C_1-C_{12})$-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The elucidations relating to the expression —$(C_1-C_{12})$-alkyl also apply to the alkyl groups in —O—$(C_1-C_{12})$-alkyl, i.e. in —$(C_1-C_{12})$-alkoxy. Preferably, these groups are unsubstituted straight-chain or branched —$(C_1-C_6)$-alkoxy groups.

Substituted —$(C_1-C_{12})$-alkyl groups and substituted —$(C_1-C_{12})$-alkoxy groups may have one or more substituents, depending on their chain length. The substituents are preferably each independently selected from —$(C_3-C_{12})$-cycloalkyl, —$(C_3-C_{12})$-heterocycloalkyl, —$(C_6-C_{20})$-aryl, fluorine, chlorine, cyano, formyl, acyl and alkoxycarbonyl.

The expression "—$(C_3-C_{12})$-cycloalkyl", in the context of the present invention, encompasses mono-, bi- or tricyclic hydrocarbyl radicals having 3 to 12, especially 5 to 12, carbon atoms. These include cyclopropyl, cyclobutyl, cyclopentyl, cyclohexyl, cycloheptyl, cyclooctyl, cyclododecyl, cyclopentadecyl, norbonyl and adamantyl.

One example of a substituted cycloalkyl would be menthyl.

The expression "—$(C_3-C_{12})$-heterocycloalkyl groups", in the context of the present invention, encompasses nonaromatic saturated or partly unsaturated cycloaliphatic groups having 3 to 12, especially 5 to 12, carbon atoms. The —$(C_3-C_{12})$-heterocycloalkyl groups have preferably 3 to 8, more preferably 5 or 6, ring atoms. In the heterocycloalkyl groups, as opposed to the cycloalkyl groups, 1, 2, 3 or 4 of the ring carbon atoms are replaced by heteroatoms or heteroatom-containing groups. The heteroatoms or the heteroatom-containing groups are preferably selected from —O—, —S—, —N—, —N(=O)—, —C(=O)— and —S(=O)—. Examples of —$(C_3-C_{12})$-heterocycloalkyl groups are tetrahydrothiophenyl, tetrahydrofuryl, tetrahydropyranyl and dioxanyl.

In the context of the present invention, the expression "—$(C_6-C_{20})$-aryl and —$(C_6-C_{20})$-aryl-$(C_6-C_{20})$-aryl-" encompasses mono- or polycyclic aromatic hydrocarbyl radicals. These have 6 to 20 ring atoms, more preferably 6 to 14 ring atoms, especially 6 to 10 ring atoms. Aryl is preferably —$(C_6-C_{10})$-aryl and —$(C_6-C_{10})$-aryl-$(C_6-C_{10})$-aryl-. Aryl is especially phenyl, naphthyl, indenyl, fluorenyl, anthracenyl, phenanthrenyl, naphthacenyl, chrysenyl, pyrenyl, coronenyl. More particularly, aryl is phenyl, naphthyl and anthracenyl.

Substituted —$(C_6-C_{20})$-aryl groups and —$(C_6-C_{20})$-aryl-$(C_6-C_{20})$-aryl groups may have one or more (e.g. 1, 2, 3, 4 or 5) substituents, depending on the ring size. These substituents are preferably each independently selected from —H, —$(C_1-C_{12})$-alkyl, —O—$(C_1-C_{12})$-alkyl, —O—$(C_6-C_{20})$-aryl, —$(C_6-C_{20})$-aryl, -halogen (such as Cl, F, Br, I), —COO—$(C_1-C_{12})$-alkyl, —CONH—$(C_1-C_{12})$-alkyl, —$(C_6-C_{20})$-aryl-CON[$(C_1-C_{12})$-alkyl]$_2$, —CO—$(C_1-C_{12})$-alkyl, —CO—$(C_6-C_{20})$-aryl, —COOH, —OH. —SO$_3$H, —SO$_3$Na, —NO$_2$, —CN, —N[$(C_1-C_{12})$-alkyl]$_2$.

Substituted —$(C_6-C_{20})$-aryl groups and —$(C_6-C_{20})$-aryl-$(C_6-C_{20})$-aryl groups are preferably substituted —$(C_6-C_{10})$-aryl groups and —$(C_6-C_{10})$-aryl-$(C_6-C_{10})$-aryl groups, especially substituted phenyl or substituted naphthyl or substituted anthracenyl. Substituted —$(C_6-C_{20})$-aryl groups preferably bear one or more, for example 1, 2, 3, 4 or 5, substituents selected from —$(C_1-C_{12})$-alkyl groups, —$(C_1-C_{12})$-alkoxy groups.

The expression "halogens" encompasses Cl, F, Br, I, preferably Cl, Br, I.

Sulphonyl groups are understood to mean the following groups:

$$\begin{array}{c} O \\ \| \\ -S-Y \\ \| \\ O \end{array}$$

with Y=OH, halogens, alkyl, aryl, cycloalkyl, where the radicals include the abovementioned definitions and may also be substituted.

Sulphenyl groups are understood to mean the following groups:

$$-S-Z$$

with Z=OH, halogens, alkyl, aryl, cycloalkyl with Z≠H, where the radicals include the abovementioned definitions and may also be substituted.

In one embodiment, $X^1$ is selected from:
tert-butyloxycarbonyl, methyloxycarbonyl, benzyloxycarbonyl, phenyloxycarbonyl, trifluoroacetyl, benzoyl.

In one embodiment, $X^2$ is selected from:
tert-butyloxycarbonyl, methyloxycarbonyl, benzyloxycarbonyl, phenyloxycarbonyl, acetyl, trifluoroacetyl, benzoyl.

In one embodiment, $X^3$ is selected from:
methyloxycarbonyl, benzyloxycarbonyl, phenyloxycarbonyl, acetyl, trifluoroacetyl, benzoyl.

In one embodiment, $X^1$ is selected from:
tert-butyloxycarbonyl, methyloxycarbonyl, benzyloxycarbonyl, phenyloxycarbonyl, benzoyl.

In one embodiment, $X^2$ is selected from:
tert-butyloxycarbonyl, methyloxycarbonyl, benzyloxycarbonyl, phenyloxycarbonyl, acetyl, benzoyl.

In one embodiment, $X^3$ is selected from:
methyloxycarbonyl, benzyloxycarbonyl, phenyloxycarbonyl, acetyl, benzoyl.

In one embodiment, $R^1$, $R^2$, $R^3$, $R^4$, $R^{1'}$, $R^{2'}$, $R^{3'}$, $R^{4'}$ are selected from:
—H, —($C_1$-$C_{12}$)-alkyl, —O—($C_1$-$C_{12}$)-alkyl, —O—($C_6$-$C_{20}$)-aryl, —S-alkyl, —S-aryl, halogen.

In one embodiment, $R^1$, $R^2$, $R^3$, $R^4$, $R^{1'}$, $R^{2'}$, $R^{3'}$, $R^{4'}$ are selected from:
—H, —($C_1$-$C_{12}$)-alkyl, —O—($C_1$-$C_{12}$)-alkyl, —O—($C_6$-$C_{20}$)-aryl.

In one embodiment, $R^{5'}$, $R^{6'}$, $R^{7'}$, $R^{8'}$, $R^{9'}$, $R^{10'}$ are selected from:
—H, —($C_1$-$C_{12}$)-alkyl, —O—($C_1$-$C_{12}$)-alkyl, —O—($C_6$-$C_{20}$)-aryl, —S-alkyl, —S-aryl, halogen.

In one embodiment, $R^{5'}$, $R^{6'}$, $R^{7'}$, $R^{8'}$, $R^{9'}$, $R^{10'}$ are selected from:
—H, —($C_1$-$C_{12}$)-alkyl, —O—($C_1$-$C_{12}$)-alkyl, —O—($C_6$-$C_{20}$)-aryl.

In one embodiment, $R^5$, $R^6$, $R^7$, $R^8$, $R^9$, $R^{10}$ are selected from: —H, —($C_1$-$C_{12}$)-alkyl, —O—($C_1$-$C_{12}$)-alkyl, —O—($C_6$-$C_{20}$)-aryl, —S-alkyl, —S-aryl, halogen.

In one embodiment, $R^5$, $R^6$, $R^7$, $R^8$, $R^9$, $R^{10}$ are selected from:
—H, —($C_1$-$C_{12}$)-alkyl, —O—($C_1$-$C_{12}$)-alkyl, —O—($C_6$-$C_{20}$)-aryl.

In one embodiment, the compound has the general structure (I).

In one embodiment, the compound has the general structure (II).

In one embodiment, the compound has the general structure (III).

As well as the compounds, a process for the preparation of 2,2'-diaminobiaryls is also claimed.

Process for preparing 2,2'-diaminobiaryls, comprising the process steps of:
a) reacting a compound of the formula (IVa) or (Va):

(IVa)

(Va)

with reaction of (IVa) with $X^{11}$ or $X^{12}$ to give (IVb1) or (IVb2), or
reaction of (Va) with $X^{13}$ to give (Vb):

(IVb1)

(IVb2)

(Vb)

b) reacting a compound of the formula (VIa) or (VIIa):

(VIa)

(VIIa)

with reaction of (VIa) with $X^{11}$ to give (VIb), or
of (VIIa) with $X^{12}$ or $X^{13}$ to give (VIIb1) or (VIIb2):

c) electrochemical coupling of:
(IVb1) with (VIb) to give (I*), or
(IVb2) with (VIIb1) to give (II*), or
(Vb) with (VIIb2) to give (III*), in each case with use of the compound having the higher oxidation potential in excess:

where
$R^{11}$, $R^{12}$, $R^{13}$, $R^{14}$, $R^{11'}$, $R^{12'}$, $R^{13'}$, $R^{14'}$ are selected from:
—H, —($C_1$-$C_{12}$)-alkyl, —O—($C_1$-$C_{12}$)-alkyl, —O—($C_6$-$C_{20}$)-aryl, —($C_6$-$C_{20}$)-aryl, —S-alkyl, —S-aryl, halogen, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl. —COOH, —OH, —$SO_3H$, —CN, —N[($C_1$-$C_{12}$)-alkyl]$_2$;
$R^{15}$, $R^{16}$, $R^{17}$, $R^{18}$, $R^{19}$, $R^{20}$, $R^{15'}$, $R^{16'}$, $R^{17'}$, $R^{18'}$, $R^{19'}$, $R^{20'}$ are selected from:
—H, —($C_1$-$C_{12}$)-alkyl, —O—($C_1$-$C_{12}$)-alkyl, —O—($C_6$-$C_{20}$)-aryl, —($C_6$-$C_{20}$)-aryl, —S-alkyl, —S-aryl, halogen, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —COOH, —OH, —$SO_3H$, —N[($C_1$-$C_{12}$)-alkyl]$_2$;
where the alkyl and aryl groups mentioned may be substituted;
$X^{11}$, $X^{12}$, $X^{13}$ are selected from:
tert-butyloxycarbonyl, methyloxycarbonyl, benzyloxycarbonyl, phenyloxycarbonyl, acetyl, trifluoroacetyl, benzoyl, sulphonyl, sulphenyl.

By electrochemical coupling, biaryldiamines are prepared without having to add organic oxidizing agents, work with exclusion of moisture or maintain anaerobic reaction regimes. This direct method of C,C coupling opens up an inexpensive and environmentally benign alternative to existing multistage conventionally organic synthesis routes.

The process specified here does not have the disadvantages discussed in connection with J.-F. Cui, H. Huang, H. Wong, Synlett 2011, 7, 1018-1022.

In one variant of the process, $X^{11}$, $X^{12}$, $X^{13}$ are selected from:
tert-butyloxycarbonyl, methyloxycarbonyl, benzyloxycarbonyl, phenyloxycarbonyl, acetyl, trifluoroacetyl, benzoyl.

In one variant of the process, $X^{11}$ is selected from:
tert-butyloxycarbonyl, methyloxycarbonyl, benzyloxycarbonyl, phenyloxycarbonyl, trifluoroacetyl, benzoyl.

In one variant of the process, $X^{12}$ is selected from:
tert-butyloxycarbonyl, methyloxycarbonyl, benzyloxycarbonyl, phenyloxycarbonyl, acetyl, trifluoroacetyl, benzoyl.

In one variant of the process, $X^{13}$ is selected from:
methyloxycarbonyl, benzyloxycarbonyl, phenyloxycarbonyl, acetyl, trifluoroacetyl, benzoyl.

In one variant of the process, $X^{11}$ is selected from:
tert-butyloxycarbonyl, methyloxycarbonyl, benzyloxycarbonyl, phenyloxycarbonyl, benzoyl.

In one variant of the process, $X^{12}$ is selected from:
tert-butyloxycarbonyl, methyloxycarbonyl, benzyloxycarbonyl, phenyloxycarbonyl, acetyl, benzoyl.

In one variant of the process, $X^{13}$ is selected from:
methyloxycarbonyl, benzyloxycarbonyl, phenyloxycarbonyl, acetyl, benzoyl.

In one variant of the process, $R^1$, $R^2$, $R^3$, $R^4$, $R^{1'}$, $R^{2'}$, $R^{3'}$, $R^{4'}$ are selected from:

—H, —($C_1$-$C_{12}$)-alkyl, —O—($C_1$-$C_{12}$)alkyl, —O—($C_6$-$C_{20}$)-aryl, —S-alkyl, —S-aryl, halogen.

In one variant of the process, $R^1$, $R^2$, $R^3$, $R^4$, $R^{1'}$, $R^{2'}$, $R^{3'}$, $R^{4'}$ are selected from:

—H, —($C_1$-$C_{12}$)-alkyl, —O—($C_1$-$C_{12}$)-alkyl, —O—($C_6$-$C_{20}$)-aryl.

In one variant of the process, $R^{5'}$, $R^{6'}$, $R^{7'}$, $R^{8'}$, $R^{9'}$, $R^{10'}$ are selected from:

—H, —($C_1$-$C_{12}$)-alkyl, —O—($C_1$-$C_{12}$)-alkyl, —O—($C_6$-$C_{20}$)-aryl, —S-alkyl, —S-aryl, halogen.

In one variant of the process, $R^{5'}$, $R^{6'}$, $R^{7'}$, $R^{8'}$, $R^{9'}$, $R^{10'}$ are selected from:

—H, —($C_1$-$C_{12}$)-alkyl, —O—($C_1$-$C_{12}$)-alkyl, —O—($C_6$-$C_{20}$)-aryl.

In one variant of the process, $R^5$, $R^6$, $R^7$, $R^8$, $R^9$, $R^{10}$ are selected from:

—H, —($C_1$-$C_{12}$)-alkyl, —O—($C_1$-$C_{12}$)-alkyl, —O—($C_6$-$C_{20}$)-aryl, —S-alkyl, —S-aryl, halogen.

In one variant of the process, $R^5$, $R^6$, $R^7$, $R^8$, $R^9$, $R^{10}$ are selected from.

—H, —($C_1$-$C_{12}$)-alkyl, —O—($C_1$-$C_{12}$)-alkyl. —O—($C_6$-$C_{20}$)-aryl.

By electrochemical coupling (process step c)), biaryldiamines are prepared without having to add organic oxidizing agents, work with exclusion of moisture or maintain anaerobic reaction conditions. This direct method of C,C coupling opens up an inexpensive and environmentally beneficial alternative to existing multistage conventionally organic synthesis routes, since it enables both the avoidance of wastes and the reduction of the consumption of scarce raw materials (metals).

Process step c) can be conducted using different carbon electrodes (glassy carbon, boron-doped diamond, graphites, carbon fibres, nanotubes, inter alia), metal oxide electrodes and metal electrodes. This involves applying current densities in the range of 1-50 mA/cm$^2$.

The electrochemical coupling (process step c)) is conducted in the customary, known electrolysis cells.

In one variant of the process, the second aminoaryl is used in at least twice the amount compared to the first aminoaryl.

In one variant of the process, the ratio of the first aminoaryl to the second aminoaryl is in the range from 1:2 to 1:4.

If required, a conductive salt can be added to the reaction.

In one variant of the process, the conductive salt is selected from the group of the alkali metal, alkaline earth metal, tetra($C_1$-$C_6$-alkyl)ammonium,1,3-di($C_1$-$C_6$-alkyl)imidazolium and tetra($C_1$-$C_6$-alkyl)phosphonium salts.

In one variant of the process, the counterions of the conductive salts are selected from the group of sulphate, hydrogensulphate, alkylsulphates, arylsulphates, alkylsulphonates, arylsulphonates, halides, phosphates, carbonates, alkylphosphates, alkylcarbonates, nitrate, tetrafluoroborate, hexafluorophosphate, hexafluorosilicate, fluoride and perchlorate.

In one variant of the process, the conductive salt is selected from tetra-($C_1$-$C_6$-alkyl)ammonium salts, and the counterion is selected from sulphate, alkylsulphate, arylsulphate.

The workup and recovery of the biaryldiamines is very simple and is effected, after the reaction has ended, by generally standard separation methods. First of all, the electrolyte solution is distilled and the individual compounds are obtained separately in the form of different fractions. A further purification can be effected, for example, by crystallization, distillation, sublimation or chromatography.

A problem that occurs in the electrochemical coupling of different molecules is that the co-reactants generally have different oxidation potentials $E_{Ox}$. The result of this is that the molecule having the lower oxidation potential has a higher propensity to release an electron (e$^-$) to the anode and an H$^+$ ion to the solvent, for example, than the molecule having the lower oxidation potential. The oxidation potential $E_{Ox}$ can be calculated via the Nernst equation:

$$E_{Ox} = E° + (0.059/n)*lg([Ox]/[Red])$$

$E_{Ox}$: Electrode potential for the oxidation reaction (=oxidation potential)
E°: Standard electrode potential
n: Number of electrons transferred
[Ox]: Concentration of the oxidized form
[Red]: Concentration of the reduced form

The oxidation potentials of the respective aniline and/or naphthylamine derivatives depend both on the protecting group used in each case and on the structure of the substrate itself. According to the protecting group used, a change in the oxidation potential by several hundred millivolts is possible. This adjustment of the oxidation potentials is possible via electron-withdrawing or electron-donating groups, but also via different sizes and the associated steric effects. The process according to the invention thus for the first time opens up an additional means of controlling the oxidation potential of the aniline and naphthylamine derivatives via the protecting groups.

In addition, it is possible to shift the oxidation potentials of the substrates used through the controlled addition of protic additives such as methanol or water to the electrolyte (such as HFIP: 1,1,1,3,3,3-hexafluoro-2-propanol).

The invention is illustrated in detail hereinafter by working examples and figures.

Figure 1:
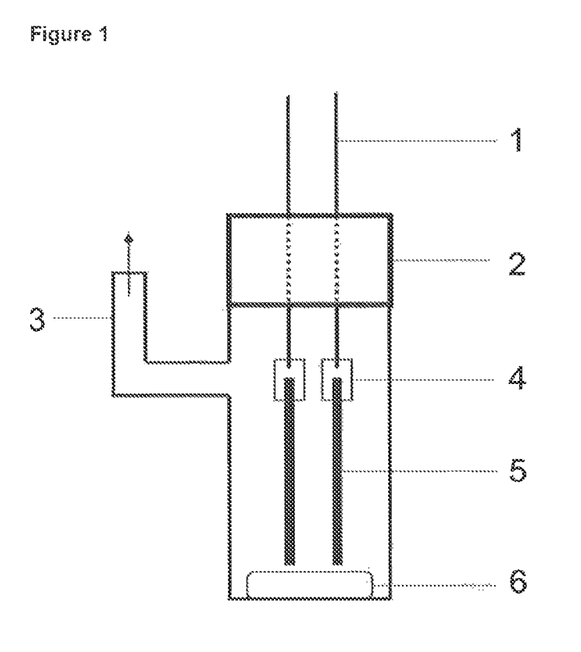

FIG. 1 shows the schematic setup of a reaction apparatus in which the coupling reaction to give the corresponding unsymmetric 2,2'-diaminobiaryls can be conducted. The reaction apparatus comprises glassy carbon electrodes (5) held with stainless steel clamps (4). A magnetic stirrer bar (6) ensures mixing in the reaction apparatus. A Teflon stopper (2) rests on top of the reaction apparatus, through which stainless steel holders (1) for the electrodes lead. The reaction apparatus, a beaker cell here, has a fitted outlet (3) for a reflux condenser attachment.

Figure 2:
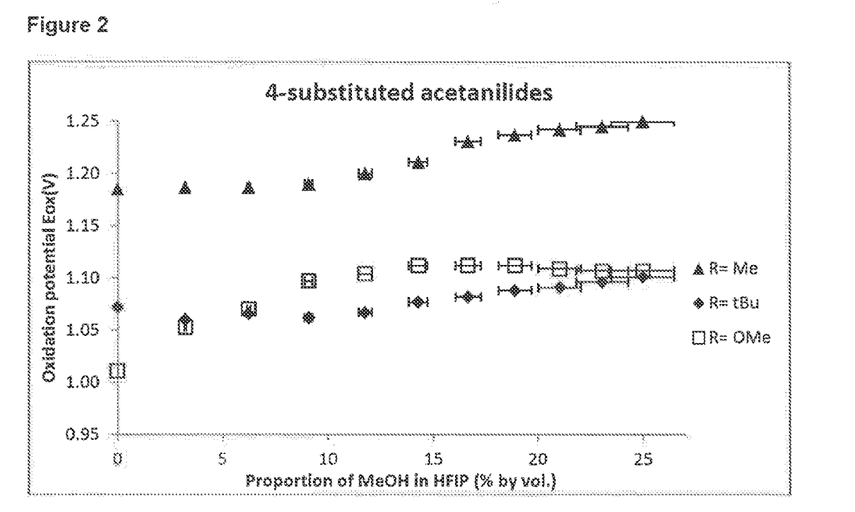

FIG. 2: $E_{Ox}$ as a function of the para substituents of acetanilides

In general, through addition of methanol, a rise in $E_{ox}$ of 4-substituted acetanilides is observed. It is noticeable here that $E_{ox}$ of 4-methoxyacetanilide on addition of about 8% by volume of MeOH is actually raised above $E_{ox}$ of 4-tert-butylacetanilide. A rise in E by up to 100 mV is possible in a selective manner.

Figure 3:
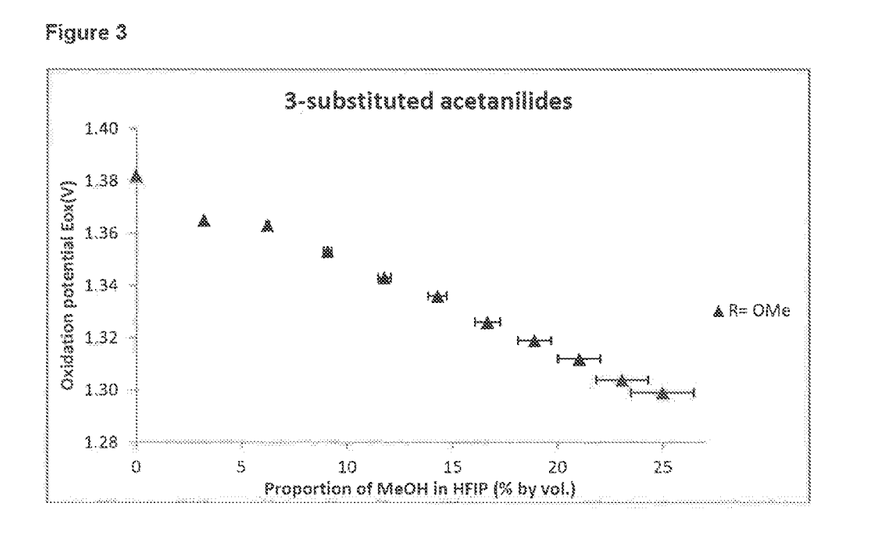

FIG. 3: $E_{Ox}$ as a function of the meta substituents of acetanilides

The addition of methanol to meta-substituted acetanilides, shown here using the example of 3-methoxyacetanilide, leads to a virtually linear decrease in $E_{ox}$. A drop of 80 mV has been measured here.

Figure 4:
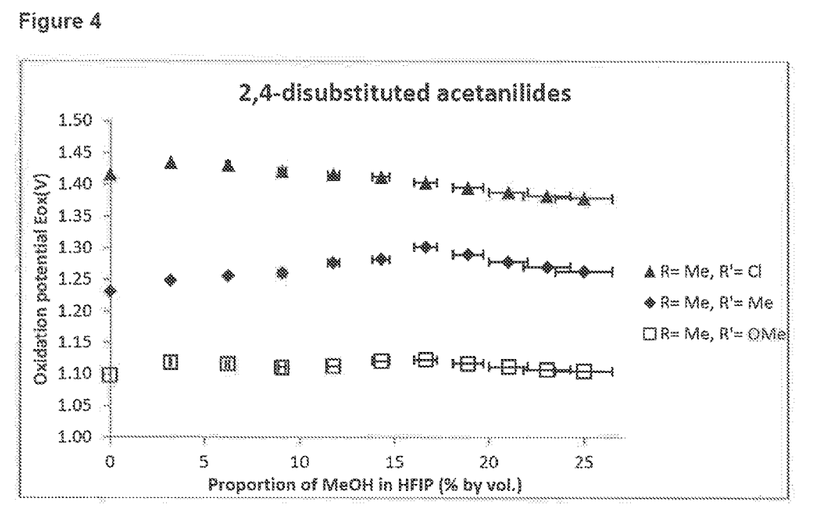

FIG. 4: $E_{Ox}$ as a function of the ortho,para substituents of acetanilide

The changes in $E_{ox}$ in the case of 2,4 disubstitution only have a weak effect on acetanilides. Only a slight rise (R=R'=Me) or drop (R=Me, R'=Cl) in $E_{ox}$ can be observed. Addition of methanol in the case of this substitution pattern causes a variation in the oxidation potentials by about 30 mV.

Figure 5:
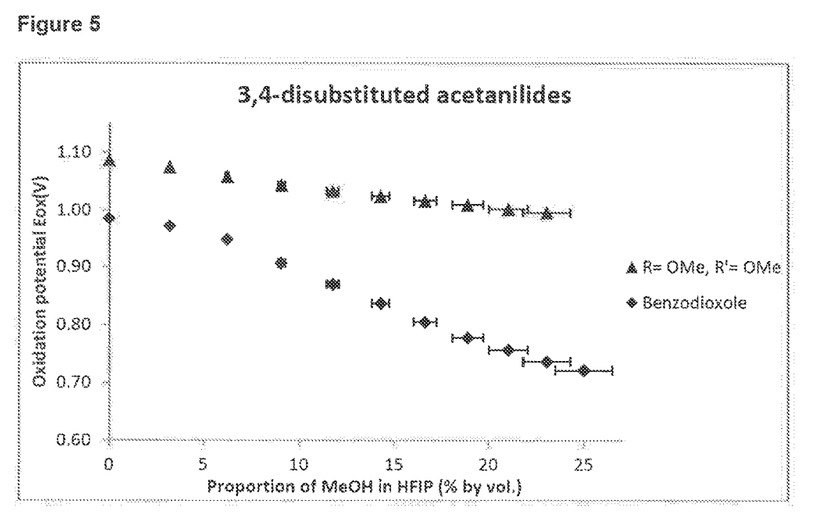

FIG. 5: $E_{Ox}$ as a function of the meta,para substituents of acetanilides In contrast, a significant lowering in $E_{ox}$ is possible when using a 3,4 disubstitution. It is found here that the substrate having the higher electron density (a benzodioxole derivative) experiences a distinct drop by almost 300 mV.

Figure 6:
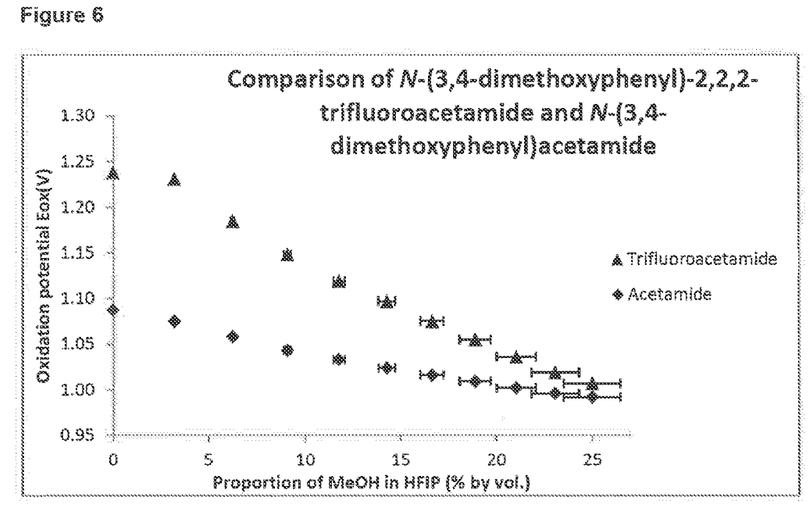

FIG. 6: Comparison of $E_{Ox}$ as a function of the protection of 3,4-dimethoxyaniline The use of trifluoroacetyl rather than acetyl protecting groups, as a result of strong electron withdrawal by the fluorine atoms, causes a rise in $E_{ox}$ of 3,4-dimethoxyaniline by about 150 mV. At the same time, the influence of MeOH on the trifluoroacetyl derivative is considerably enhanced. The latter derivative, in 1,1,1,3,3,3-hexafluoro-2-propanol (HFIP), experiences a drop of up to 250 mV in the case of addition of MeOH.

Figure 7:
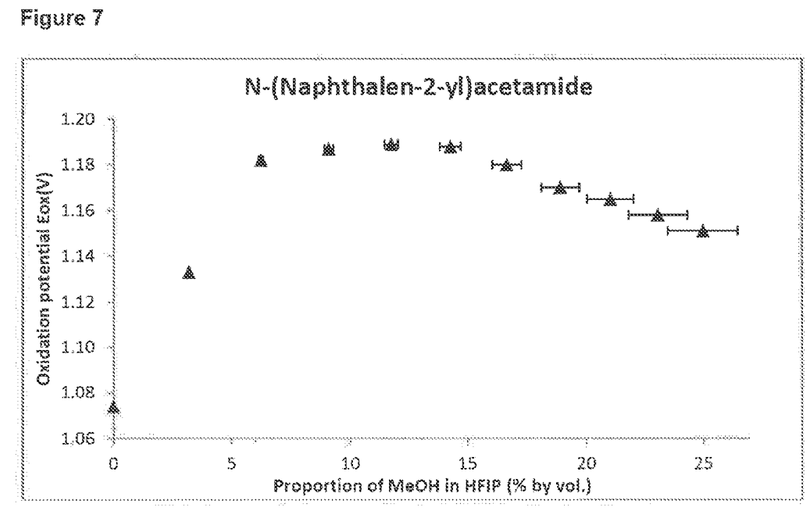

FIG. 7: $E_{Ox}$ as a function of N-(naphthalen-2-yl)acetamide

N-(Naphthalen-2-yl)acetamide shows a similar plot to p-methoxyacetanilide. Addition of methanol results in a distinct rise in $E_{ox}$ to about 15% by volume. A shift of about 140 mV is possible in this way. In the case of greater amounts of MeOH, there is a drop in $E_{ox}$ here too.

On the basis of the results shown in FIGS. 2-7, it becomes clear that the oxidation potentials can be influenced by the different protecting groups and hence the electrochemical coupling can be controlled.

Analysis

Chromatography

The preparative liquid chromatography separations via flash chromatography were conducted with a maximum pressure of 1.6 bar on 60 M silica gel (0.040-0.063 mm) from Macherey-Nagel GmbH & Co. Düren. The unpressurized separations were conducted on Geduran Si 60 silica gel (0.063-0.200 mm) from Merck KGaA, Darmstadt. The solvents used as eluents (ethyl acetate (technical grade), cyclohexane (technical grade)) had been purified by distillation beforehand on a rotary evaporator.

For thin-film chromatography (TLC), ready-made PSC silica gel 60 F254 plates from Merck KGaA, Darmstadt were used. The Rf values are reported as a function of the eluent mixture used. The TLC plates were stained using a cerium/molybdatophosphoric acid solution as immersion reagent. Cerium/molybdatophosphoric acid reagent: 5.6 g of molybdatophosphoric acid, 2.2 g of cerium(IV) sulphate tetrahydrate and 13.3 g of concentrated sulphuric acid to 200 ml of water.

Gas Chromatography (GC/GCMS)

The gas chromatography studies (GC) on product mixtures and pure substances were effected with the aid of the GC-2010 gas chromatograph from Shimadzu, Japan. Analysis is effected on an HP-5 quartz capillary column from Agilent Technologies, USA (length: 30 m; internal diameter: 0.25 mm; film thickness of the covalently bound stationary phase: 0.25 µm; carrier gas: hydrogen; injector temperature: 250° C.; detector temperature: 310° C.; program: "hard" method: start temperature 50° C. for 1 min, heating rate: 15° C./min, end temperature 290° C. for 8 min). Gas chromatography-mass spectrometry analyses (GC-MS) of product mixtures and pure substances were conducted with the aid of the GC-2010 gas chromatograph combined with the GCMS-QP2010 mass detector from Shimadzu, Japan. Analysis is effected on an HP-1 quartz capillary column from Agilent Technologies, USA (length: 30 m; internal diameter 0.25 mm; film thickness of the covalently bound stationary phase: 0.25 µm; carrier gas: hydrogen; injector temperature: 250° C.; detector temperature: 310° C.; program: "hard" method: start temperature 50° C. for 1 min, heating rate: 15° C./min, end temperature 290° C. for 8 min; GC-MS: ion source temperature: 200° C.).

Melting Points

Melting points were measured with the aid of the SG 2000 melting point determination instrument from HW5, Mainz, and are uncorrected.

Elemental Analysis

The elemental analyses were conducted in the analytical division of the Organic Chemistry department of the Johannes Gutenberg University of Mainz on a Vario EL Cube from Foss-Heraeus, Hanau.

Mass Spectrometry

All electrospray ionization analyses (ESI+) were conducted on a QT of Ultima 3 from Waters Micromasses, Milford, Mass. EI mass spectra and the high-resolution EI spectra were analysed on an instrument of the MAT 95 XL sector field instrument type from ThermoFinnigan, Bremen.

NMR Spectroscopy

The NMR spectroscopy studies were conducted on multinucleus resonance spectrometers of the AC 300 or AV II 400 type from Bruker, Analytische Messtechnik, Karlsruhe. The solvent used was CDCl3. The 1H and 13C spectra were calibrated according to the residual content of undeuterated solvent using the NMR Solvent Data Chart from Cambridge Isotopes Laboratories, USA. Some of the 1H and 13C signals were assigned with the aid of H,H-COSY, H,H-NOESY, H,C-HSQC and H,C-HMBC spectra. The chemical shifts are reported as δ values in ppm. For the multiplicities of the NMR signals, the following abbreviations were used: s (singlet), bs (broad singlet), d (doublet), t (triplet), q (quartet), m (multiplet), dd (doublet of doublets), dt (doublet of triplets), tq (triplet of quartets). All coupling constants J were reported in hertz (Hz) together with the number of bonds covered. The numbering given in the assignment of signals corresponds to the numbering shown in the formula schemes, which do not necessarily have to correspond to IUPAC nomenclature.

Examples of Possible Protecting Groups:
Carbamates tertbutyloxycarbonyl (Boc)

Methyloxycarbonyl

Benzyloxycarbonyl (Cbz)

Phenyloxycarbonyl

Amides:

Acetyl

Trifluoroacetyl

Benzoyl

Sulphonyl

Sulphenyl with Bn=benzyl, Ph=phenyl.

The Y and Z radicals correspond to the definition given above.

The introduction of the protecting groups can be effected, for example, as described in P. G. M. Wuts, T. W. Greene "Greene's Protective Groups in Organic Synthesis", fourth edition, 2007, John Wiley and Sons; Hoboken, N.J.

M1: Method for N-acetylation

The aniline derivative or naphthylamine derivative to be protected (1 equiv.) is initially charged in a round-bottom flask and dissolved in dichloromethane. While cooling with ice, 1.2 equiv. of acetic anhydride are gradually added dropwise to the reaction solution. On completion of addition, the reaction mixture is stirred at room temperature and/or under reflux for 24 hours. After the reaction has ended, the solvent is removed under reduced pressure and the crude product is purified by flash chromatography on silica gel 60 in the eluent CH:EA (4:1 to 1:1).

M2: Method for N-2,2,2-Trifluoroacetamide Protection

A round-bottom flask is initially charged with the aniline derivative or naphthylamine derivative to be protected (1 equiv.) in dichloromethane solution. While cooling with ice and stirring vigorously, 1.2 equiv. of trifluoroacetic anhydride are added gradually to this solution. After the addition has ended, the reaction flask is heated to 35° C. for 4-5 hours. After the reaction has ended, the solvent is removed under reduced pressure and the crude product is purified by flash chromatography on silica gel 60 in the eluent CH:EA (4:1 to 1:1).

M3: Method for Electrochemical Cross-Coupling

In an undivided beaker cell having glassy carbon electrodes, 3.8 mmol of component A (cf. Reaction Scheme 2) and 7.6 mmol of component B to be coupled (cf. Reaction Scheme 2) are dissolved in 25 ml of 1,1,1,3,3,3-hexafluoroisopropanol and 0.77 g of MTBS. The electrolysis is galvanostatic. During the electrolysis, the beaker cell is heated to 50° C. with the aid of a water bath and the reaction mixture is stirred. After the electrolysis has ended, the cell contents are transferred to a corresponding round-bottom flask and the solvent is removed on a rotary evaporator at 50° C., 200→90 mbar, under reduced pressure.

Electrode Material:
Anode: glassy carbon
Cathode: glassy carbon
Electrolysis Conditions:
Temperature [T]: 50° C.
Current density [j]: 2.8 mA/cm2
Charge [Q]: 2 F (per deficiency component)

M4: Method for Electrochemical Cross-Coupling (Screening)

In an undivided screening cell, 0.76 mmol of component A (cf. Reaction Scheme 2) and 1.51 mmol of component B to be coupled (cf. Reaction Scheme 2) were dissolved in 5 ml of 1,1,1,3,3,3-hexafluoroisopropanol and 154 mg of MTBS. The electrolysis is galvanostatic. During the electrolysis, the screening cell is heated to 50° C. in a screening block and the reaction mixture is stirred. After the electrolysis has ended, the cell contents are transferred to a corresponding round-bottom flask and the solvent is removed on a rotary evaporator at 50° C., 200→90 mbar, under reduced pressure.

Electrode Material:
Anode: BDD or glassy carbon
Cathode; BDD or glassy carbon
Electrolysis Conditions:
Temperature [T]: 50° C.
Current density [j]: 2.8 mA/cm2
Charge [Q]: 2 F (per deficiency component)

M5: General Method for Removal of N-2,2,2-Trifluoroacetamide Protecting Groups A round-bottom flask is initially charged with 1 equiv. of the substrate to be deprotected, dissolved in a methanol/water mixture in a ratio of 2:1. Then 10 equiv. of potassium carbonate are added to the reaction solution, which is stirred at room temperature for four days. After the reaction has ended, the solvent is removed under reduced pressure. The residue is slurried with water and the deprotected product is extracted with dichloromethane. Unless deprotection is quantitative, the crude product is purified by flash chromatography on silica gel 60.

M6: General Method for Removal of N-Acetyl Protecting Groups

The substrate to be deprotected (1 equiv.) is initially charged in a round-bottom flask and dissolved in methanol. While stirring vigorously, 12 equiv. of boron trifluoride diethyl etherate are added to the reaction solution, and then the mixture is heated under reflux for 18 hours. The reaction is ended by addition of 20 equiv. of triethylamine, and the product which precipitates out in solid form can be filtered off.

2-(N-Acetyl)amino-1-(2'-(N'-trifluoroacetyl)amino-4',5'-dimethoxyphenyl)naphthalene a) Synthesis of 2,2'-Diaminobiaryl on the Screening Scale The electrolysis is conducted according to M4 in an undivided screening cell. For this purpose, 140 mg (0.76 mmol, 1.0 equiv.) of N-(naphthalen-2-yl)acetamide and 377 mg (1.51 mmol, 2 equiv.) of N-(3,4-dimethoxyphenyl)-2,2,2-trifluoroacetamide are dissolved in 5 ml of 1,1,1,3,3,3-hexafluoro-2-propanol (HFIP), 154 mg of MTBS are added and the electrolyte is transferred into the electrolysis cell. After the electrolysis, the solvent and unconverted reactants are removed under reduced pressure. The crude product is then purified by flash chromatography on silica gel 60 in a 2:1 eluent (CH:EA), and the product is obtained as a colourless solid.

The screening reaction was used to examine different electrode materials. The electrode materials chosen were BDD and glassy carbon, which prepared the C,C cross-coupling product in different yields (Table 1).

TABLE 1

List of the electrode materials used with the resulting yields

| Electrode material | Yield |
|---|---|
| BDD | 24% (78 mg) |
| glassy carbon | 44% (144 mg) |

Electrode material Yield
BDD 24% (78 mg)
Glassy carbon 44% (144 mg)

b) Synthesis of 2,2'-Diaminobiaryl in a Beaker Cell

The electrolysis is conducted according to M3 in an undivided beaker cell with glassy carbon electrodes. 0.70 g (3.79 mmol, 1.0 equiv.) of N-(naphthalen-2-yl)acetamide and 1.89 g (7.57 mmol, 2 equiv.) of N-(3,4-dimethoxyphenyl)-2,2,2-trifluoroacetamide are dissolved in 25 ml of 1,1,1,3,3,3-hexafluoro-2-propanol (HFIP), 0.77 g of MTBS are added and the electrolyte is transferred into the electrolysis cell. The solvent and unconverted amounts of reactant are removed under reduced pressure after the electrolysis, the crude product is purified by flash chromatography on silica gel 60 in a 2:1 eluent (CH:EA) and the product is obtained as a colourless solid.

Yield: 1.02 g (62%, 2.36 mmol)
GC (hard method, HP-5): tR=16.90 min
Rf (EA:CH=2:1)=0.5
$^1$H NMR (300 MHz, CDCl3) δ=2.00 (s, 3H), 3.84 (s, 3H), 4.01 (s, 3H), 6.73 (s, 1H), 7.15 (bs, 1H), 7.27 (d, J=9 Hz, 1H), 7.44 (dt, J=6 Hz, 7.66 (s, 1H), 7.91 (m, 3H) 7.93 (bs, 1H), 8.11 (d, 1H)
$^{13}$C NMR (75 MHz, CDCl3) δ=24.23, 56.33, 56.38, 107.73, 113.15, 113.63, 117.45, 120.79, 122.57, 124.55, 124.88, 125.96, 127.03, 127.54, 128.47, 130.08, 131.51, 132.36, 133.98, 148.10, 149.53, 169.47
HRMS for $C_{22}H_{19}F3N_2O_4$(ESI+) [M+H+]: calc.: 433.1375, found: 433.1375.

2-(N-Acetyl)amino-1-(2'-amino-4',5'-dimethoxyphenyl)naphthalene

In a round-bottom flask, according to M5, 0.65 g (1.50 mmol, 1 equiv.) of 2-(N-acetyl)amino-1-(2'-(N'-trifluoroacetyl)-amino-4',5'-dimethoxyphenyl)naphthalene is dissolved in 120 ml of a methanol/water mixture in a ratio of 2:1, 2.07 g (15.01 mmol, 10 equiv.) of potassium carbonate are added to this solution and the reaction mixture is stirred at room temperature for four days. After the reaction has ended, the solvent is removed under reduced pressure, the residue is slurried with water and the deprotected product is extracted with dichloromethane.

Yield: 500 mg (99%, 1.49 mmol)
GC (hard method, HP-5): tR=18.68 min
Rf (EA:CH=2:1)=0.46
$^1$H NMR (300 MHz, CDCl3) δ=2.03 (s, 3H), 3.12 (bs, 2H), 3.77 (s, 3H), 3.94 (s, 3H), 6.59 (d, J=15 Hz, 2H), 7.35-7.46 (m, 4H), 7.87 (dd, J=9 Hz, 2H), 8.40 (d, J=9 Hz, 1H)
$^{13}$C NMR (75 MHz, CDCl3) δ=24.87, 56.02, 56.58, 101.21, 111.55, 114.60, 121.36, 123.50, 125.18, 125.61, 126.81, 128.25, 129.01, 131.28, 132.77, 134.48, 137.70, 143.04, 150.28, 168.96

2-(N-Acetyl)amino-1-(2'-(N'-4-methylphenylsulphonyl))amino-4',5'-dimethoxyphenyl)naphthalene 278 mg (0.83 mmol, 1 equiv.) of N-acetyl-2-amino-1-(2'-amino-4',5'-dimethoxyphenyl)naphthalene in 110 ml of dichloromethane are initially charged in a round-bottom flask. Added to this reaction solution are 173 mg (0.91 mmol, 1.1 equiv.) of p-methylsulphonyl chloride and 0.13 ml (0.91 mmol, 1.1 equiv.) of triethylamine, and the mixture is stirred at room temperature for 111 hours. After the reaction has ended, the solvent is removed under reduced pressure and the crude product is purified by flash chromatography on silica gel 60 in a 2:1 eluent (CH:EA).

Yield: 342 mg (84%, 0.70 mmol)
GC (hard method, HP-5): tR=16.87 min
Rf (EA:CH=2:1)=0.21
$^1$H NMR (300 MHz, CDCl3) δ=1.87 (s, 3H), 2.38 (s, 3H), 3.75 (s, 3H), 3.94 (s, 3H), 6.09 (s, 1H), 6.56 (s, 1H), 6.68 (s, 1H), 6.94 (d, J=9 Hz, 1H), 7.10 (d, J=6 Hz, 2H), 7.24 (t, J=6 Hz, 1H), 7.29 (bs, 1H), 7.36 (d, J=9 Hz, 2H), 7.42 (t, J=6 Hz, 1H), 7.88 (dd, J=15 Hz, J=9 Hz, 2H), 8.32 (d, J=9 Hz, 1H)
$^{13}$C NMR (75 MHz, CDCl3) δ=21.70, 24.58, 56.19, 56.27, 106.87, 113.17, 119.35, 121.46, 124.49, 124.89, 125.40, 125.92, 127.40, 127.40, 127.44, 128.50, 129.74, 129.74, 129.81, 130.98, 132.28, 134.61, 136.40, 144.15, 147.38, 149.75, 168.58
HRMS for $C_{20}H_{20}N_2O_3$(ESI+) [M+H+]: calc.: 491.1641, found: 491.1651.

2-Amino-1-(2'-N-(4-methylphenylsulphonyl)-amino-4,5'-dimethoxyphenyl)naphthalene According to M6, 342 mg (0.70 mmol, 1 equiv.) of N-acetyl-2-amino-1-(2'-N-(4-methylphenylsulphonyl)-amino-4',5'-dimethoxyphenyl)naphthalene are initially charged in 40 ml of methanol. 1.06 ml (8.37 mmol, 12 equiv.) of boron trifluoride diethyl etherate are added to this solution while stirring vigorously, and the mixture is heated under reflux for 18 hours. The reaction is ended by the addition of 2 ml of triethylamine, and the product which precipitates out in solid form can be filtered off.

Yield: 219 mg (70%, 0.49 mmol)
GC (hard method, HP-5): tR=15.64 min
Rf (EA:CH=2:1)=0.78
$^1$H NMR (300 MHz, CDCl3) δ=2.21 (s, 3H), 3.00 (bs, 2H), 3.76 (s, 3H), 3.98 (s, 3H), 6.64 (s, 1H), 6.73-6.83 (m, 4H), 7.00-7.08 (m, 2H), 7.15-7.24 (m, 3H), 7.40 (s, 1H), 7.70 (dd, J=6 Hz, J=9 Hz, 2H)
$^{13}$C NMR (75 MHz, CDCl3) δ=21.61, 56.18, 56.27, 108.18, 114.19, 114.95, 118.02, 120.61, 122.65, 123.75, 126.88, 126.98, 126.98, 128.08, 128.34, 128.49, 129.25, 129.25, 130.04, 133.51, 135.97, 140.54, 143.28, 147.20, 149.30
HRMS for $C_{20}H_{20}N_2O_3$(ESI+) [M+H+]: calc.: 449.1535, found: 449.1542.

2-Amino-1-(2'-N-(4-methylphenylsulphonyl)-amino-4'5'-dimethoxyphenyl)naphthalene In a round-bottom flask, 300 mg (0.69 mmol, 1 equiv.) of 2-(N-acetyl)amino-1-(2'-(N'-trifluoroacetyl)-amino-4',5'-dimethoxyphenyl)naphthalene are dissolved in 80 ml of hydrazine hydrate solution (80% aqueous solution). The reaction solution is stirred under reflux at 120° C. for 4 days. After the reaction has ended, the mixture is extracted 3 times with 20 ml of dichloromethane each time, and the solvent is removed under reduced pressure. The product is obtained as a brownish foam.

Yield: 200 mg (98%, 0.68 mmol)
GC (hard method, HP-5): tR=17.21 min
Rf (EA:CH=2:1)=0.44
$^1$H NMR (300 MHz, CDCl3) δ=3.61 (s, 3H), 3.77 (s, 3H), 4.01 (bs, 2H), 4.77 (bs, 2H), 6.50 (s, 1H), 6.58 (s, 1H), 7.09-7.25 (m, 4H), 7.66 (d, J=9 Hz, 1H), 7.69 (d, J=6 Hz, 1H)
$^{13}$C NMR (75 MHz, CDCl3) δ=55.25, 56.37, 100.60, 111.34, 113.66, 116.07, 118.46, 120.99, 123.45, 125.97, 127.07, 127.88, 128.19, 133.70, 140.43, 140.84, 143.58, 149.32
HRMS for $C_{18}H_{18}N_2O_2$ (ESI+) [M+H+]: calc.: 295.1447, found: 295.1458.

The compounds shown in the examples solve the stated problem. It has been possible for the first time to prepare novel 2,2'-diaminobiaryls in good to very good yields. At the same time, an entirely novel synthesis strategy is employed: Both aminoaryls are first protected independently, then electrochemically coupled, and can then be selectively deprotected if required. Through this procedure, it is possible to prepare compounds having two identical protecting groups which were unobtainable because of the existing procedure specified in the prior art.

The invention claimed is:

1. A process for preparing 2,2'-diaminobiaryls, comprising:

a) reacting a compound of the formula (IVa) or (Va):

(IVa)

(Va)

with reaction of (IVa) with $X^{11}$ or $X^{12}$ to give (IVb1) or (IVb2), or of (Va) with $X^{13}$ to give (Vb):

(IVb1)

(IVb2)

(Vb)

b) reacting a compound of the formula (VIa) or (VIIa):

(VIa)

(VIIa)

with reaction of (VIa) with $X^{11}$ to give (VIb), or of (VIIa) with $X^{12}$ or $X^{13}$ to give (VIIb1) or (VIIb2):

(VIb)

(VIIb1)

(VIIb2)

c) electrochemical coupling of:
  (IVb1) with (VIb) to give (1*), or
  (IVb2) with (VIIb1) to give (11*), or
  (Vb) with (VIIb2) to give (III*),
in each case in a suitable electrolyte medium where the compound having the higher oxidation potential is present in excess:

(I*)

(II*)

(III*)

where $R^{11}$, $R^{12}$, $R^{13}$, $R^{14}$, $R^{11'}$, $R^{12'}$, $R^{11'}$, $R^{14'}$ are selected from the group consisting of:

—H, —$(C_1-C_{12})$-alkyl, —O—$(C_1-C_{12})$-alkyl, —O—$(C_1-C_{20})$-aryl, —$(C_6-C_{20})$-aryl, —S-alkyl, —S-aryl, halogen, —COO—$(C_1-C_{12})$-alkyl, —CONH—$(C_1-C_{12})$-alkyl, —CO—$(C_1-C_{12})$-alkyl, —CO—$(C_6-C_{20})$-aryl, —COOH, —OH, —$SO_3H$, —CN, and —N[$(C_1-C_{12})$-alkyl]2;

$R^{15}$, $R^{16}$, $R^{17}$, $R^{18}$, $R^{19}$, $R^{20}$, $R^{15'}$, $R^{16'}$, $R^{17'}$, $R^{1'}$, $R^{1'}$, $R^2$ are selected from the group consisting of:

—H, —$(C_1-C_{12})$-alkyl, —O—$(C_1-C_{12})$-alkyl, —O—$(C_6-C_{20})$-aryl, —$(C_6-C_{20})$-aryl, —S-alkyl, —S-aryl, halogen, —COO—$(C_1-C_{12})$-alkyl, —CONH—$(C_1-C_{12})$-alkyl, —CO—$(C_1-C_{12})$-alkyl, —CO—$(C_6-C_{20})$-aryl, —COOH, —OH, —$SO_3H$, and —N[$(C_1-C_{12})$-alkyl]$_2$;

where the alkyl and aryl groups mentioned may be substituted;

$X^{11}$, $X^{12}$, $X^{13}$ are selected from:

tert-butyloxycarbonyl, methyloxycarbonyl, benzyloxycarbonyl, phenyloxycarbonyl, acetyl, trifluoroacetyl, benzoyl, sulphonyl, and sulphenyl.

* * * * *